(12) United States Patent
Ko et al.

(10) Patent No.: US 11,987,781 B2
(45) Date of Patent: May 21, 2024

(54) GAS COLLECTION DEVICE

(71) Applicant: LG Chem, Ltd., Seoul (KR)

(72) Inventors: Eun Byeol Ko, Daejeon (KR); Jung Hye Won, Daejeon (KR); Nak Hee Choi, Daejeon (KR); Ji Seok Lee, Daejeon (KR); Eun Yeong Jin, Daejeon (KR); Hae Sung Yun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 303 days.

(21) Appl. No.: 17/360,585

(22) Filed: Jun. 28, 2021

(65) Prior Publication Data

US 2022/0002648 A1    Jan. 6, 2022

(30) Foreign Application Priority Data

Jul. 2, 2020   (KR) .................. 10-2020-0081741
Dec. 8, 2020   (KR) .................. 10-2020-0170281

(51) Int. Cl.
| | | |
|---|---|---|
| C12M 1/107 | (2006.01) | |
| C12M 1/00 | (2006.01) | |
| C12M 1/04 | (2006.01) | |
| C12M 1/24 | (2006.01) | |
| C12M 1/34 | (2006.01) | |

(52) U.S. Cl.
CPC ............ C12M 23/36 (2013.01); C12M 23/08 (2013.01); C12M 23/38 (2013.01); C12M 29/00 (2013.01);

(Continued)

(58) Field of Classification Search
USPC ...................................... 435/287.5
See application file for complete search history.

(56) References Cited

U.S. PATENT DOCUMENTS 5,621,180 A * 4/1997 Simon ............... G01N 1/24
                                                73/863.23
6,180,397 B1 * 1/2001 Binder .................. C12M 41/34
                                                435/303.1

(Continued)

FOREIGN PATENT DOCUMENTS

CN   103243022 A  *  8/2013  ............ C12M 21/04
CN   105754851 A  *  7/2016
(Continued)

OTHER PUBLICATIONS

Document entitled CN105754851A Biological aroma generating and enriching device, machine translation of CN 105754851A provided by Espacenet (Year: 2016).*

(Continued)

*Primary Examiner* — Holly Kipouros
(74) *Attorney, Agent, or Firm* — Lerner David LLP

(57) ABSTRACT

The present invention relates to a gas collection device and is directed to a gas collection device for collecting a gas which is generated while microorganisms are cultured in a super absorbent polymer product. The gas collection device may comprise a constant temperature chamber having an interior that is configured to be maintained at a set temperature; a culture flask unit located inside the constant temperature chamber and configured to culture a bacteria therein; an adsorption unit located outside the constant temperature chamber and configured to receive a gas inside the culture flask unit; a pump unit connected to a rear end of the adsorption unit and configured to suck the gas inside the culture flask unit into the adsorption unit; and a mass flow controller located outside the constant temperature chamber and configured to control a flow rate of the gas sucked into the adsorption unit.

10 Claims, 3 Drawing Sheets

(52) U.S. Cl.
CPC ............ *C12M 41/14* (2013.01); *C12M 41/34* (2013.01); *C12M 41/46* (2013.01)

(56) References Cited

U.S. PATENT DOCUMENTS

| | | | |
|---|---|---|---|
| 8,569,050 B1 * | 10/2013 | Ericsson | C12M 21/02 |
| | | | 435/292.1 |
| 10,738,141 B2 | 8/2020 | Loick et al. | |
| 2009/0152744 A1 * | 6/2009 | Mou | C12M 27/20 |
| | | | 261/119.1 |
| 2014/0120610 A1 * | 5/2014 | Yamashita | C12M 37/02 |
| | | | 435/297.2 |
| 2016/0168527 A1 * | 6/2016 | Lee | C12M 41/48 |
| | | | 435/303.1 |

FOREIGN PATENT DOCUMENTS

| | | | |
|---|---|---|---|
| CN | 110358669 A * | 10/2019 | ............ C12M 21/02 |
| JP | H07120112 A | 5/1995 | |
| JP | H10-038790 A | 2/1998 | |
| JP | 2007-101337 A | 4/2007 | |
| KR | 10-2004-0089318 A | 10/2004 | |
| KR | 200396829 Y1 | 9/2005 | |
| KR | 100525515 B1 | 11/2005 | |
| KR | 100569724 B1 | 4/2006 | |
| KR | 10-1250898 A | 4/2013 | |
| KR | 101420082 B1 | 7/2014 | |
| KR | 101740114 B1 | 5/2017 | |
| KR | 10-1991325 B | 6/2019 | |

OTHER PUBLICATIONS

Kino-Oka et al., Characterization and Application of Plant Hairy Roots Endowed with Photosynthetic Functions, 2001, Advances in Biochemical Engineering/Biotechnology, vol. 72 (Year: 2001).*

Ahmed et al., Development of an adaptable headspace sampling method for metabolic profiling of the fungal volatome, 2018, Analyst, 143, 4155-4162 (Year: 2018).*

* cited by examiner

GAS COLLECTION DEVICE

TECHNICAL FIELD

The present application claims the benefit of priority of Korean Patent Application No. 10-2020-0081741 filed on Jul. 2, 2020, and all contents disclosed in that patent document are hereby incorporated by reference herein as a part of this specification.

The present invention relates to a gas collection device, and is directed to a gas collection device for collecting a gas which is generated while microorganisms are cultured in a super absorbent polymer product.

BACKGROUND OF THE INVENTION

In general, adult diapers and the like are worn for a long time when they are used, which may generate odor components as microorganisms are cultured by an urine. Accordingly, a product such as the adult diaper can be made of a super absorbent polymer having an antibacterial function.

In order to develop a super absorbent polymer product having the antibacterial function, studies have been conducted to reduce the odor components by controlling a degree of cultivation of the microorganisms in the super absorbent polymer.

For this purpose, it has been required to develop a technology for checking a reduction effect on the odor components generated by the microorganisms in the super absorbent polymer, specifically, a technology for quantitatively collecting the odor components.

An analysis method performed using an oil bath in the prior art has poor reproducibility and quantification, and thus a new analysis technique improved has been needed.

SUMMARY OF THE INVENTION

The present invention relates to a gas collection device, and is to provide a gas collection device for collecting a gas which is generated while microorganisms are cultured in a super absorbent polymer product.

The technical problems to be achieved by the present invention are not limited to the technical problems mentioned above, and other technical problems that are not mentioned will be able to be clearly understood by a person who has an ordinary knowledge in the technical field to which the present invention belongs from the following description.

The gas collection device of the present invention may comprise a constant temperature chamber whose interior is maintained at a set temperature; a culture flask unit located inside the constant temperature chamber and culturing bacteria therein; an adsorption unit located outside the constant temperature chamber and receiving a gas inside the culture flask unit; a pump unit connected to a rear end of the adsorption unit to suck the gas inside the culture flask unit into the adsorption unit; and a mass flow controller located outside the constant temperature chamber and controlling a flow rate of the gas sucked to the adsorption unit.

In the gas collection device of the present invention, the mass flow controller may be located at a rear end of the culture flask unit and a front end of the adsorption unit, and control the flow rate of the gas flowing from the culture flask unit to the adsorption unit.

The gas collection device of the present invention may further comprise an injection flow path that is a passage through which an air inside the constant temperature chamber flows into the culture flask unit; and a discharge flow path that is a passage through which the gas inside the culture flask unit flows to the mass flow controller.

The injection flow path in the gas collection device of the present invention may be provided with a check valve for preventing backflow of an air, when the air inside the constant temperature chamber flows into the culture flask unit.

In the gas collection device of the present invention, the check valve may be mounted on an inner side wall of the constant temperature chamber, wherein one end of the injection flow path may be coupled to the check valve, and the other end of the injection flow path may be coupled to the culture flask unit.

In the gas collection device of the present invention, the mass flow controller is mounted on an outer side wall of the constant temperature chamber, and the discharge flow path may include a first discharge flow path penetrating the wall of the constant temperature chamber, a second discharge flow path connecting the first discharge flow path and the culture flask unit inside the constant temperature chamber, and a third discharge flow path connecting the first discharge flow path and the mass flow controller outside the constant temperature chamber.

In the gas collection device of the present invention, the first discharge flow path may be formed of a stainless-steel tube, and the second discharge flow path may be formed of a tube made of at least one of a silicon material, a Teflon material and a PVC material. For example, the second discharge flow path may be formed of a Tygon tube.

The culture flask unit in the gas collection device of the present invention may include a container unit for accommodating an analysis target material therein and culturing the bacteria from the analysis target material, a stopper covering an opening located in the container unit, an injection tube formed to penetrate the stopper and connected to the injection flow path, and a discharge tube formed to penetrates the stopper and connected to the discharge flow path.

In the gas collection device of the present invention, the first discharge flow path may be fitted to one end of the second discharge flow path, and the injection tube and the discharge tube may be formed of the stainless-steel tube.

In the gas collection device of the present invention, a vent hole through which an air inside and outside the constant temperature chamber is vented may be located on one side wall of the constant temperature chamber, and a filter portion for filtering particles in the air may be located in the vent hole.

In the gas collection device of the present invention, the culture flask unit, the mass flow controller, and the adsorption unit may be provided in a plurality respectively, each of the plurality of culture flask units may be provided with the mass flow controller and the adsorption unit individually, and the plurality of culture flask units may be located inside one constant temperature chamber.

Effect of the Invention

The gas collection device of the present invention is a system that has airtightness without leakage even in an experiment performed for a long time, and can collect a gas component, which is generated in real time under air flow, into the adsorption unit by continuously supplying and discharging an air.

The gas collection device of the present invention is capable of continuously generating the air flow, and collect the gas content without limitation for a collection time regardless of a capacity of the culture flask unit.

The gas collection device of the present invention enables precise control and metering of a flow rate by the mass flow controller, and easy control of environmental conditions such as a culture time or temperature, so that the number of cultured bacteria and the quantitative analysis according to the antibacterial and deodorant treatment of the super absorbent polymer can be carried out precisely.

DETAILED DESCRIPTION

Figure 1:
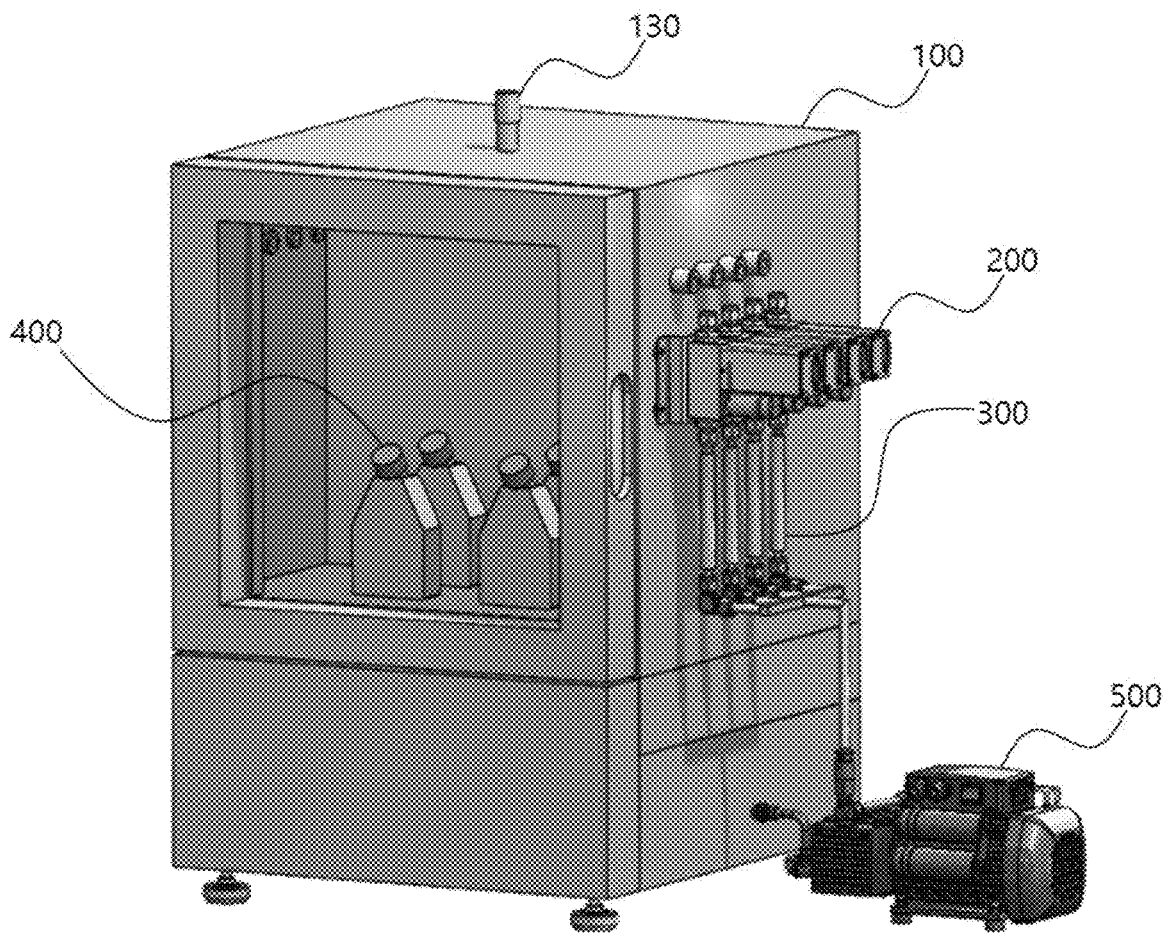
FIG. 1 is a perspective view showing a gas collection device of the present invention.

Hereinafter, embodiments of the present invention will be described in detail with reference to the accompanying drawings. In this process, sizes or shapes of constitutive elements illustrated in the drawings may be exaggerated for clarity and convenience of the explanation. Further, terms specifically defined in consideration of the configuration and operation of the present invention may vary according to the intention or custom of users or operators. Definitions of these terms should be made based on the contents throughout the present specification.

In the description of the present invention, it should be noted that the orientation or positional relationship indicated by the terms "center", "upper", "lower", "left", "right", "vertical", "horizontal", "inner side", "outer side", "one surface", "other surface", and the like is based on the orientation or positional relationship shown in the drawings, or the orientation or positional relationship arranged when the product of the present invention is usually used. Accordingly, it should not be construed that those terms limit the present invention, because they are merely for description and brief description of the present invention and are not presented on the premise that the displayed device or element must be constructed or operated in a specific orientation.

Figure 2:
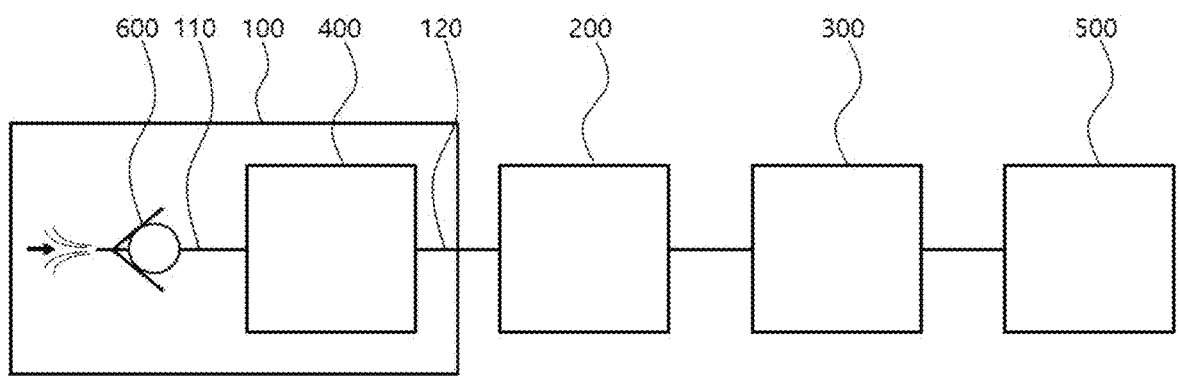
FIG. 2 is a block diagram showing a gas collection device of the present invention.
Figure 3:
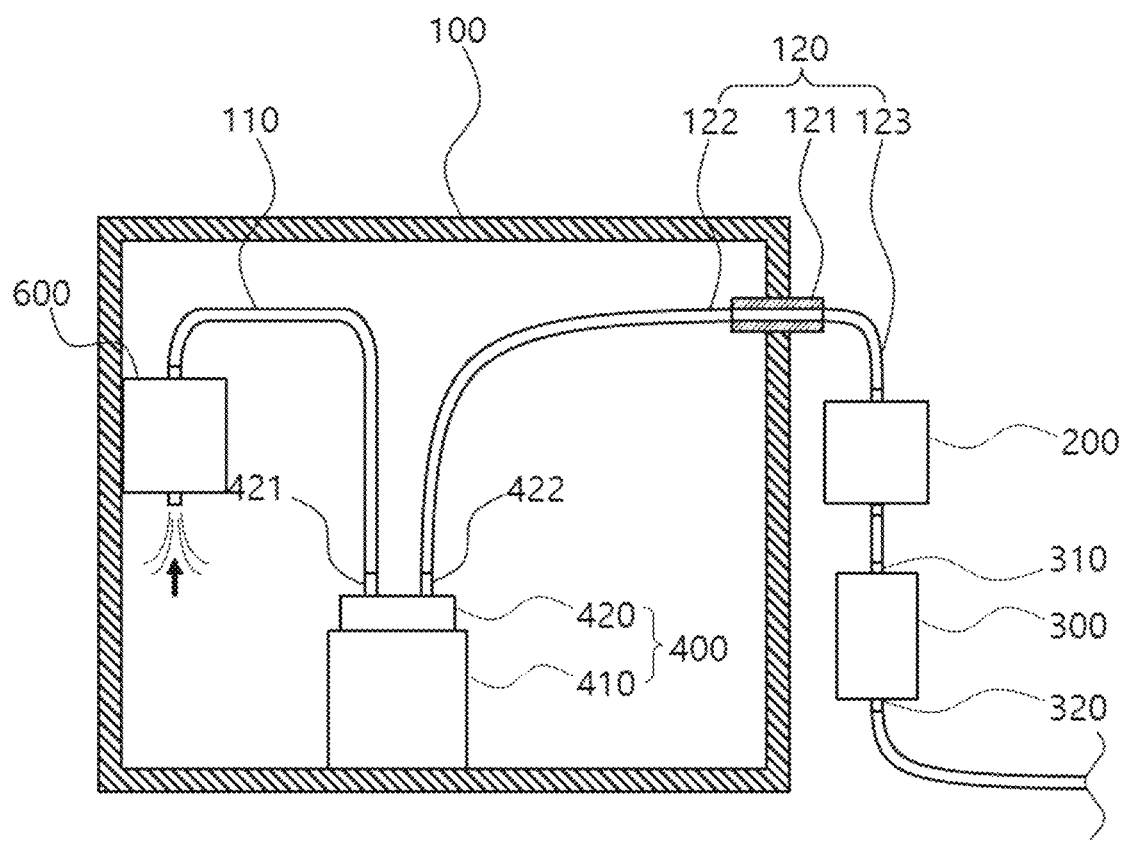
FIG. 3 is a conceptual diagram showing a culture flask unit, a check valve, and a mass flow controller.
Figure 4:
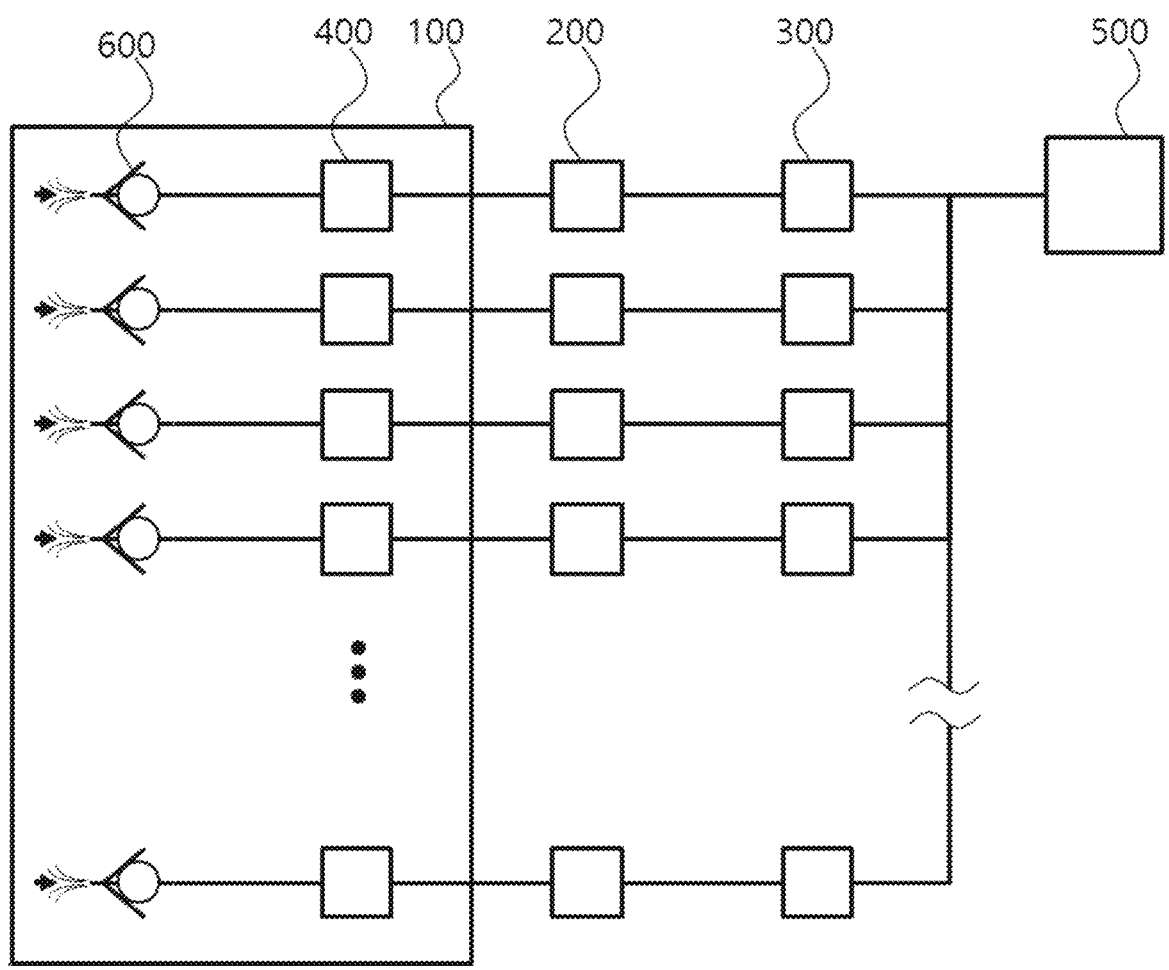
FIG. 4 is a block diagram showing another embodiment of a gas collection device of the present invention.

FIG. 1 is a perspective view showing a gas collection device of the present invention. FIG. 2 is a block diagram showing a gas collection device of the present invention. FIG. 3 is a conceptual diagram showing a culture flask unit 400, a check valve 600, and a mass flow controller 200. FIG. 4 is a block diagram showing another embodiment of a gas collection device of the present invention.

Hereinafter, the gas collection device of the present invention will be described in detail with reference to FIGS. 1 to 4.

The gas collection device of the present invention is a system that has airtightness without leakage even in an experiment performed for a long time, and can collect a gas component, which is generated in real time under air flow, into an adsorption unit 300 by continuously supplying and discharging an air.

The gas collection device of the present invention enables precise control and metering of a flow rate by a mass flow controller 200, and easy control of environmental conditions such as a culture time or temperature, so that the number of cultured bacteria and the quantitative analysis according to the antibacterial and deodorant treatment of a super absorbent polymer can be carried out precisely.

As illustrated in FIGS. 1 and 2, the gas collection device of the present invention may comprise a constant temperature chamber 100 whose interior is maintained at a set temperature; a culture flask unit 400 located inside the constant temperature chamber 100 and culturing bacteria therein; an adsorption unit 300 located outside the constant temperature chamber 100 and receiving a gas inside the culture flask unit 400; a pump unit 500 connected to a rear end of the adsorption unit 300 to suck the gas inside the culture flask unit 400 into the adsorption unit 300; and a mass flow controller 200 located outside the constant temperature chamber 100 and controlling a flow rate of the gas sucked into the adsorption unit 300.

As shown in FIG. 1, the constant temperature chamber 100 has a constant temperature space into which the culture flask unit 400 is accommodated, and may be provided with a heating means capable of heating the constant temperature space. The constant temperature space of the constant temperature chamber 100 may be maintained at about 37° C. by the heating means.

The mass flow controller 200 and the adsorption unit 300 may be located outside the constant temperature chamber 100 such that they are not heated by the heating means provided in the constant temperature chamber 100. Specifically, a bracket with which the mass flow controller 200 and the adsorption unit 300 are equipped is located on an outer wall of the constant temperature chamber 100, and the mass flow controller 200 and the adsorption unit 300 can be coupled and fixed to the outer wall of the constant temperature chamber 100 by the bracket. For example, the constant temperature chamber 100 may be a rectangular parallelepiped shape having a plurality of planes, and the mass flow controller 200 and the adsorption unit 300 may be mounted on different surfaces of the outer wall surfaces of the constant temperature chamber 100.

One side surface of the constant temperature chamber 100 is formed with a door, and the door can be opened to accommodate the culture flask unit 400 in the constant temperature space. The door is formed with a transparent window through which the culture flask unit 400 accommodated in the constant temperature space can be observed from the outside of the constant temperature chamber 100.

One side surface of the other wall of the constant temperature chamber 100 is provided with a vent hole 130 through which an air is vented inside and outside the constant temperature chamber 100, and the vent hole 130 may located with a filter portion for filtering particles in the air. A temperature of the constant temperature space in the constant temperature chamber 100 is changed by the heating means, and the air in the constant temperature space may expand or contract according to a change in the temperature. In this case, the vent hole 130 may be provided to maintain a pressure in the constant temperature space in a certain range. Due to the air which is introduced and discharged through the vent hole 130, foreign substances outside the constant temperature chamber 100 may be introduced into the constant temperature chamber 100 or components inside the constant temperature chamber 100 may be discharged to the outside of the constant temperature chamber 100. The filter portion may be provided in the vent hole 130 to prevent the foreign substances or the components from being introduced into or discharged outside the constant temperature chamber 100.

Further, since the gas collection device of the present invention continuously injects the air inside the constant temperature chamber 100 into the culture flask unit 400 during gas collection, in order to prevent a pressure drop inside the constant temperature chamber 100, an air outside the constant temperature chamber 100 can be introduced into the constant temperature chamber 100 through the vent hole 130. In this case, the foreign substances contained in the air outside the constant temperature chamber 100 can be removed through the filter portion provided in the vent hole 130.

The adsorption unit 300 may include an adsorbent for adsorbing an analysis target component from the gas delivered from the culture flask unit 400, a tube for accommodating the adsorbent therein, an inlet 310 for injecting the gas of the culture flask unit 400 into the tube, and an outlet 320 for discharging a remaining air to the outside of the tube after the analysis target component of the gas is adsorbed to the adsorbent.

The adsorption unit 300 is located outside the constant temperature chamber 100 and is maintained at a low temperature (room temperature), so that the analysis target component can be more easily adsorbed to the adsorbent and the analysis target component adsorbed to the adsorbent can be minimized from being desorbed again.

The mass flow controller (MFC) 200 may measure and control flow of a gas. The mass flow controller 200 in the gas collection device of the present invention may be located between the culture flask unit 400 and the adsorption unit 300. That is, the mass flow controller 200 is located at a rear end of the culture flask unit 400 and a front end of the adsorption unit 300, and the mass flow controller 200 may control a flow rate of the gas flowing from the culture flask unit 400 to the adsorption unit 300.

The performance of the super absorbent polymer product can be determined by analyzing how much odor components are contained in a vented air under a situation where the air is vented. Therefore, the gas collection device of the present invention can continuously flow the air to the culture flask unit 400, quantify an amount of the gas that has passed through the culture flask unit 400, and then collect the odor components contained in the quantified gas. Since the gas collection device of the present invention can accurately measure and control the amount of the gas that has passed the culture flask unit 400 through the mass flow controller 200, the quantitative analysis can be accurately performed.

The gas that has passed through the culture flask unit 400 may be a gas containing the analysis target component generated from an analysis target material accommodated inside the culture flask unit 400. Specifically, the gas delivered from the culture flask unit 400 to the mass flow controller 200 may be a gas in which the air and the analysis target component are mixed. The gas collection device of the present invention controls an amount of the air to be sufficiently larger than that of the analysis target component in the gas delivered from the culture flask unit 400 to the mass flow controller 200, so that even if the analysis target component is changed, it is possible to always accurately quantify the flow rate without resetting the mass flow controller 200.

The pump unit 500 is a vacuum pump and may allow the gas of the culture flask unit 400 to flow to the adsorption unit 300 through the mass flow controller 200 by generating a negative pressure in the adsorption unit 300. Specifically, the pump unit 500 may be connected to the outlet 320 of the adsorption unit 300 to form the negative pressure inside the tube of the adsorption unit 300.

As shown in FIG. 3, the gas collection device of the present invention may further comprise an injection flow path 110 that is a passage through which the air inside the constant temperature chamber 100 flows into the culture flask unit 400; and a discharge flow path 120 that is a passage through which the gas inside the culture flask unit 400 flows to the mass flow controller 200.

The injection flow path 110 may be provided with a check valve 600 to prevent backflow of the air when the air inside the constant temperature chamber 100 flows into the culture flask unit 400. The air inside the constant temperature chamber 100 may be introduced into the culture flask unit 400 through the check valve 600 by the negative pressure generated by the pump unit 500.

Concretely, as shown in FIG. 3, the check valve 600 may be mounted on an inner side wall of the constant temperature chamber 100, wherein one end of the injection flow path 110 is coupled to the check valve 600 and the other end of the injection flow path 110 is coupled to the culture flask unit 400.

The check valve 600 may be attached and fixed to the inner side wall of the constant temperature chamber 100. Since the gas collection device of the present invention injects the air inside the constant temperature chamber 100 into the culture flask unit 400 through the check valve 600, an air heated inside the constant temperature chamber 400, rather than a low temperature (room temperature) air outside the constant temperature chamber 400, can be injected into the culture flask unit 400 through the injection flow path 110.

As shown in FIG. 3, the mass flow controller 200 is mounted on an outer side wall of the constant temperature chamber 100, and the discharge flow path 120 may include a first discharge flow path 121 penetrating a wall of the constant temperature chamber 100, a second discharge flow path 122 connecting the first discharge flow path 121 and the culture flask unit 400 inside the constant temperature chamber 100, and a third discharge flow path 123 connecting the first discharge flow path 121 and the mass flow controller 200 outside the constant temperature chamber 100. The discharge flow path 120 may be formed to couple the first discharge flow path 121, the second discharge flow path 122, and the third discharge flow path 123. The second discharge flow path 122 or the third discharge flow path 123 may be formed in a detachable structure from the first discharge flow path 121 and replaced whenever the analysis cycle changes.

For example, the first discharge flow path 121 may be formed of a stainless-steel tube, and the second discharge flow path 122 may be formed of a tube of at least one of a silicon material, a Teflon material, and a PVC material. For example, the second discharge flow path 122 may be formed of a Tygon tube.

The first discharge flow path 121 is formed by penetrating a wall of the constant temperature chamber 100, and may be made of a stainless-steel tube of a rigid material so as to prevent the air inside and outside the constant temperature chamber 100 from leaking to an installation site of the first discharge flow path 121. Since the first discharge flow path 121 is formed of the stainless-steel tube, foreign substances are not easily adsorbed so that cleaning is easy and the previous analyzed materials can be prevented from affecting the next analysis.

The culture flask unit 400 may include a container unit 410 for accommodating the analysis target material therein and culturing bacteria from the analysis target material, a stopper 420 covering an opening located in the container unit 410, an injection tube 421 formed to penetrate the stopper 420 and connected to the injection flow path 110, and a discharge tube 422 formed to penetrates the stopper 420 and connected to the discharge flow path 120.

A super absorbent polymer, an artificial urine, and a culture bacteria may be injected into the container unit 410 as the analysis target material.

One end of the third injection flow path 123 may be coupled to the first injection flow path 111, and the other end of the third injection flow path 123 may be coupled to an injection tube 421.

One end of the second discharge flow path 122 may be coupled to the first discharge flow path 121, and the other end of the second discharge flow path 122 may be coupled to a discharge tube 422.

The injection tube 421 and the discharge tube 422 may be formed of the stainless-steel tube. If the analysis is terminated, after separating the stopper 420 from the container unit 410, the stopper 420 can be washed, and the injection tube 421 and the discharge tube 422 may also be washed.

As shown in FIG. 4, the culture flask unit 400, the mass flow controller 200, and the adsorption unit 300 may be arranged in a plurality, respectively, and each of the plurality of culture flask units 400 is provided with the mass flow controller 200 and the adsorption unit 300 individually, and the plurality of culture flask units 400 may be located inside one constant temperature chamber 100.

In the gas collection device of the present invention, one culture flask unit 400, one mass flow controller 200, and one adsorption unit 300 are grouped to form one analysis line, and a plurality of analysis lines may be equipped in one constant temperature chamber 100. Accordingly, the gas collection device of the present invention can simultaneously perform a plurality of analysis experiments sharing the same analysis conditions. The check valve 600 may also be arranged in a plurality and may be assigned to each of the analysis lines individually.

The mass flow controller 200 is located for each of the plurality of analysis lines individually, so that not only the flow rate of the plurality of analysis lines can be controlled independently, but also each of the mass flow controller 200 can accurately correct an error in the flow rate that may occur for each analysis line even when the analysis is performed under the condition of the same flow rate in the plurality of analysis lines.

EXAMPLE

A sterilized disposable culture flask unit was prepared in a volumes of 650 mL. 2 g of a super absorbent polymer (SAP), 50 mL of an artificial urine, and $10^4$ CFU of a cultured bacteria (absorbance 0.45 AU, *Proteus mirabilis*) were placed in a culture flask unit, and it was sealed.

The sealed culture flask unit 400 was accommodated into the constant temperature chamber 100 having the structure shown in FIG. 1, and cultured at a temperature of 37° C. for 16 hours.

A mass flow controller 200 was set to collect a gas generated in the culture flask unit 400 to an adsorption unit 300 at a rate of 0.2 L/min for 5 minutes.

For samples under the same condition, the gas collection was further repeated twice in the same manner as above.

Table 1 below shows results of quantitative analysis of an amount of the components collected to the adsorption unit 300 by performing the gas collection three times using TD-GC/MS (JAI JTD-505IIISE/Agilent 8890, 5977B).

TABLE 1

| Odor component | 1st time (μg) | 2nd times (μg) | 3rd times (μg) | Relative standard deviation(% RSD) |
|---|---|---|---|---|
| Trimethylamine | 0.5 | 0.4 | 0.4 | 11 |
| Isovaleraldehyde | 0.3 | 0.4 | 0.4 | 13 |
| Dimethyl disulfide | 7.8 | 8.2 | 7.9 | 2 |

COMPARATIVE EXAMPLE

An injection tube and a discharge tube were connected to a culture flask unit such that an external air was injected into the culture flask unit through the injection tube and an air inside the culture flask unit was delivered to an adsorption tube through the discharge tube. The adsorption tube was connected to the discharge tube, and a flow meter and a vacuum pump were connected to a rear end of the adsorption tube.

In the same manner as in the above Example, the culture flask unit into which a super absorbent polymer, an artificial urine, and a cultured bacteria were injected was prepared. The prepared culture flask unit was accommodated in an oil bath set at a temperature of 37° C., and then maintained for 16 hours to culture microorganisms in the culture flask unit.

After culturing for 16 hours, a flow velocity of the vacuum pump connected to a rear end of the adsorption unit was set to 0.2 L/min, and a gas generated in the culture flask unit was collected in the adsorption tube for 5 minutes.

A collection amount and a collection rate were controlled based on the measured value of the flow meter mounted between the adsorption tube and the vacuum pump.

For samples under the same condition, the gas collection was further repeated twice in the same manner as above.

Table 2 below shows results of quantitative analysis of an amount of the components collected to the adsorption tube by performing the gas collection three times using TD-GC/MS (JAI JTD-505IIISE/Agilent 8890, 5977B).

TABLE 2

| Odor component | 1st time (μg) | 2nd times (μg) | 3rd times (μg) | Relative standard deviation(% RSD) |
|---|---|---|---|---|
| Trimethylamine | 2.2 | 0.9 | 1.1 | 41 |
| Isovalderaldehyde | 0.3 | 0.1 | 0.8 | 74 |
| Dimethyl disulfide | 5.8 | 3.0 | 2.4 | 70 |

From Tables 1 and 2 above, it can be seen that the results of the Examples analyzed by the gas collection device of the present invention show low relative standard deviations of 2 to 13%, whereas the results of the Comparative Examples show high relative standard deviations of 41 to 70%. Accordingly, it can be confirmed from the above that since the gas collection device according to the present invention does not require multiple verification experiments, an efficient and accurate analysis result can be obtained.

Although the embodiments according to the present invention have been described above, they are merely exemplary, and thus any person who has an ordinary knowledge in the relevant art will understand that various modifications and equivalents of those embodiments are possible from the above descriptions. Therefore, the true technical protection scope of the present invention should be determined by the following claims.

DESCRIPTION OF REFERENCE NUMERALS

100 . . . Constant temperature chamber
110 . . . Injection flow path
120 . . . Discharge flow path
121 . . . First discharge flow path
122 . . . Second discharge flow path
123 . . . Third discharge flow path
130 . . . Vent hole
200 . . . Mass flow controller
300 . . . Adsorption unit
310 . . . Inlet
320 . . . Outlet
400 . . . Culture flask unit
410 . . . Container unit
420 . . . Stopper
421 . . . Injection tube
422 . . . Discharge tube
500 . . . Pump unit
600 . . . Check valve

What is claimed:

1. A gas collection device comprising:
a constant temperature chamber having an interior that is configured to be maintained at a set temperature;
a culture flask unit located inside the constant temperature chamber and configured to culture bacteria therein;
an injection flow path that is a passage through which an air inside the constant temperature chamber is configured to flow into the culture flask unit, the injection flow path being provided with a check valve configured to prevent backflow of the air;
an adsorption unit located outside the constant temperature chamber and configured to receive a gas inside the culture flask unit;
a pump unit connected to a rear end of the adsorption unit and configured to suck the gas inside the culture flask unit into the adsorption unit;
a mass flow controller located outside the constant temperature chamber and configured to control a flow rate of the gas sucked into the adsorption unit; and
a vent hole configured to vent an air inside and outside the constant temperature chamber, the vent hole located on one side wall of the constant temperature chamber, the vent hole having a filter portion for filtering particles in the air, the vent hole configured to maintain a constant air pressure in the interior of the constant temperature chamber.

2. The gas collection device of claim 1, wherein the mass flow controller is located at a rear end of the culture flask unit and at a front end of the adsorption unit, and the mass flow controller is configured to control the flow rate of the gas flowing from the culture flask unit to the adsorption unit.

3. The gas collection device of claim 2, further comprising:
a discharge flow path that is a passage through which the gas inside the culture flask unit is configured to flow to the mass flow controller.

4. The gas collection device of claim 3, wherein the air inside the constant temperature chamber flows into the culture flask unit.

5. The gas collection device of claim 4, wherein the check valve is mounted on an inner side wall of the constant temperature chamber, one end of the injection flow path being coupled to the check valve and another end of the injection flow path being coupled to the culture flask unit.

6. The gas collection device of claim 3, wherein the mass flow controller is mounted on an outer side wall of the constant temperature chamber, and
wherein the discharge flow path includes a first discharge flow path penetrating the wall of the constant temperature chamber, a second discharge flow path connecting the first discharge flow path and the culture flask unit inside the constant temperature chamber, and a third discharge flow path connecting the first discharge flow path and the mass flow controller outside the constant temperature chamber.

7. The gas collection device of claim 6, wherein the first discharge flow path is formed of a stainless-steel tube, and the second discharge flow path is formed of a tube made of at least one of: a silicon material, a Teflon material, or a PVC material.

8. The gas collection device of claim 7, wherein the culture flask unit includes:
a container unit configured to accommodate an analysis target material therein and configured to culture the bacteria from the analysis target material,
a stopper covering an opening located in the container unit,
an injection tube penetrating the stopper and connected to the injection flow path, and
a discharge tube penetrating the stopper and connected to the discharge flow path.

9. The gas collection device of claim 8, wherein the first discharge flow path is fitted to one end of the second discharge flow path, and
wherein the injection tube and the discharge tube are formed of the stainless-steel tube.

10. The gas collection device of claim 1, wherein the culture flask unit is one of a plurality of culture flask units, the mass flow controller is one of a plurality of mass flow controllers, and the adsorption unit is one of a plurality of adsorption units,
each of the plurality of culture flask units is coupled to a corresponding one of the mass flow controllers and a corresponding one of the adsorption units, and the plurality of culture flask units is located inside of the constant temperature chamber.

* * * * *